United States Patent [19]
Griffiths

[11] Patent Number: 5,766,196
[45] Date of Patent: Jun. 16, 1998

[54] SURGICAL INSTRUMENT WITH STEERABLE DISTAL END

[75] Inventor: Jerry Richard Griffiths, Whitman, Mass.

[73] Assignee: TNCO, Inc., Whitman, Mass.

[21] Appl. No.: 739,924

[22] Filed: Oct. 30, 1996

Related U.S. Application Data

[63] Continuation of Ser. No. 254,900, Jun. 6, 1994, abandoned.
[51] Int. Cl.⁶ .................................................. H61B 17/00
[52] U.S. Cl. ........................ 606/170; 606/174; 606/705; 128/751
[58] Field of Search ........................ 606/1, 170, 171, 606/174, 51, 52, 205–210; 128/750–755

[56] References Cited

U.S. PATENT DOCUMENTS

| | | | |
|---|---|---|---|
| 4,483,562 | 11/1984 | Schoolman | 606/174 |
| 4,880,015 | 11/1989 | Nierman | 128/751 |
| 4,945,920 | 8/1990 | Clossick | 606/205 |
| 5,330,502 | 7/1994 | Hassler | 606/174 |
| 5,454,827 | 10/1995 | Aust et al. | 606/174 |

*Primary Examiner*—Michael Buiz
*Assistant Examiner*—William Lewis
*Attorney, Agent, or Firm*—Timothy J. Shea, II; Stephen Y. Chow; Harvey Kaye

[57] ABSTRACT

A medical instrument with a steerable distal end, having a handle for actuating the instrument, a distal operating section for performing a medical procedure, a middle section connecting the handle with the operating section, at least a portion of the middle section being bendable, and steerable means within the bendable portion for permitting the operating section to be controlled in direction at an angle with respect to the axis of the middle section. There are means for rotating the distal operating section into any desired angular position with respect to the longitudinal axis of the middle section. A control member control the direction of movement of the bendable section in three dimensions whereby the distal end may be positioned in any place on or off of the longitudinal axis of the middle section. A protective sheath may be disposed over the bendable section.

18 Claims, 10 Drawing Sheets

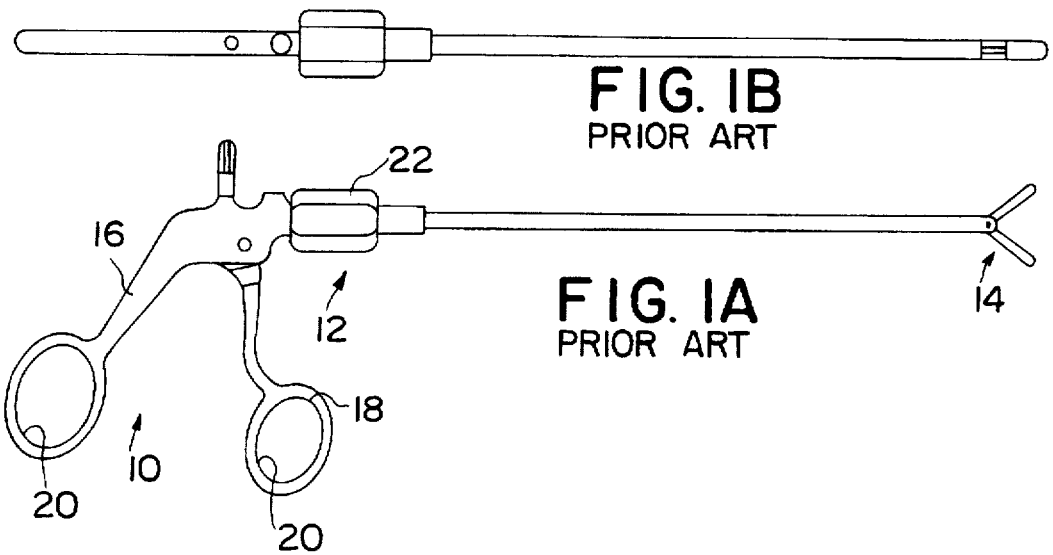
FIG. 1B PRIOR ART
FIG. 1A PRIOR ART
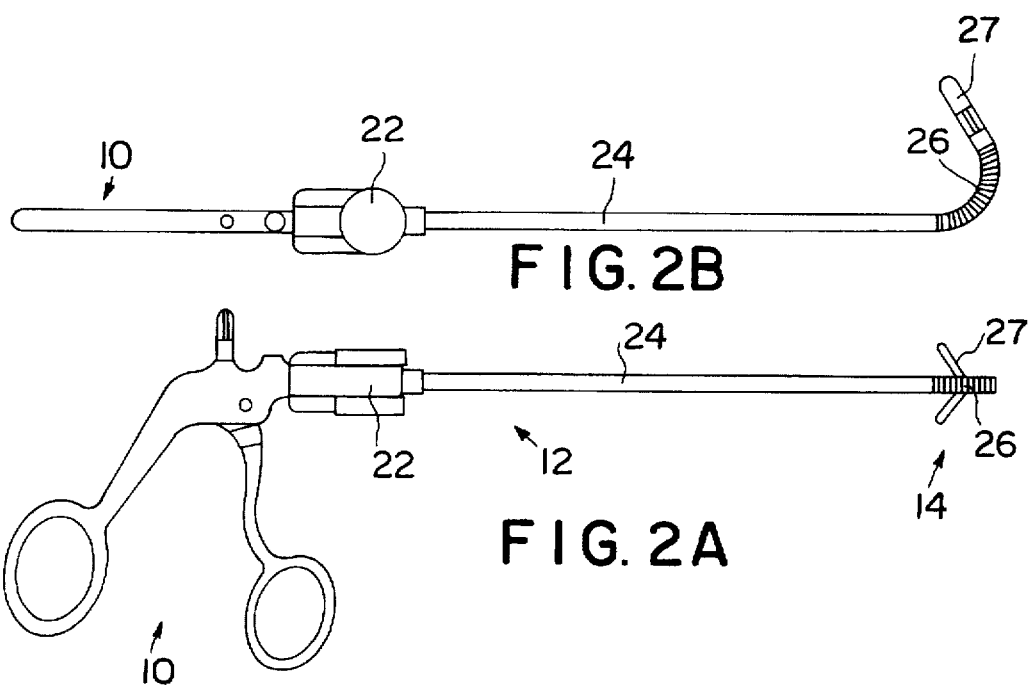
FIG. 2B
FIG. 2A

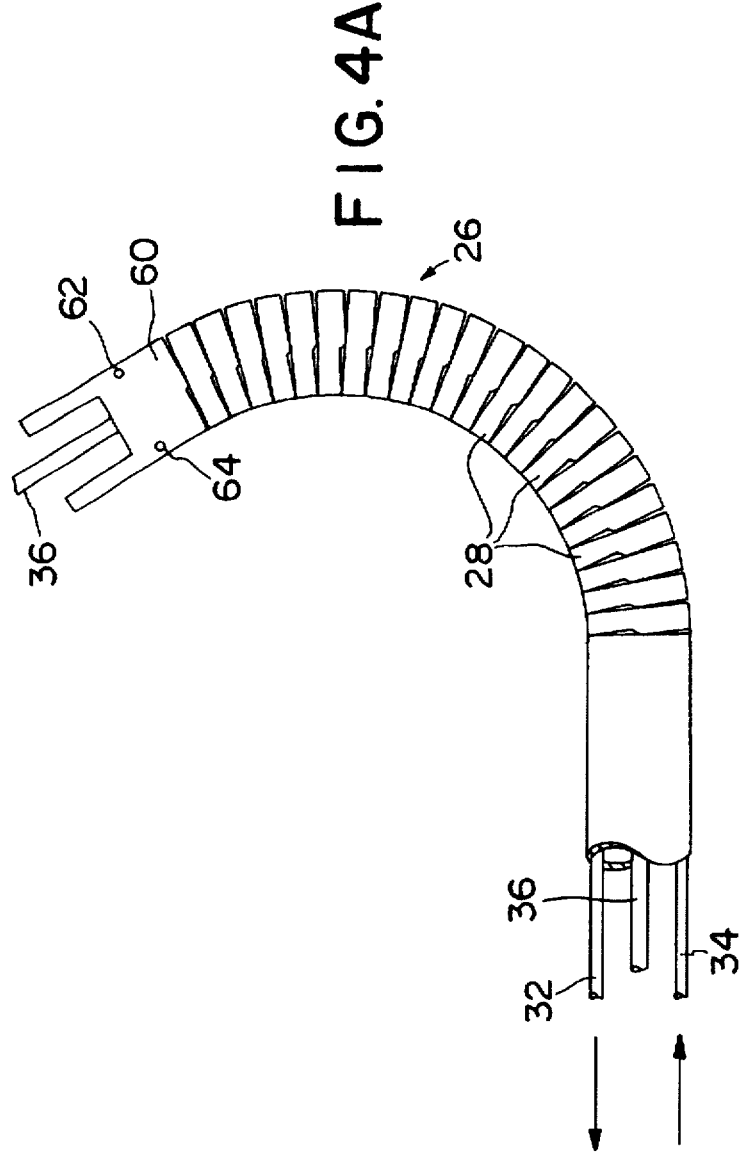
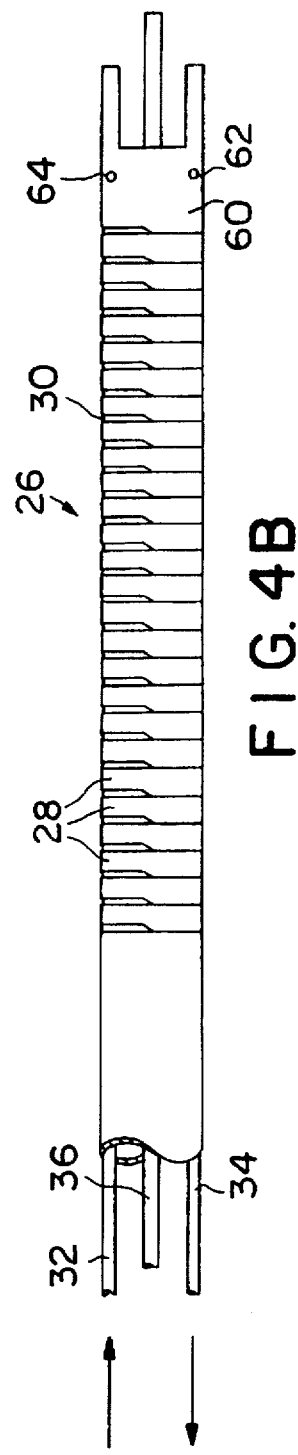

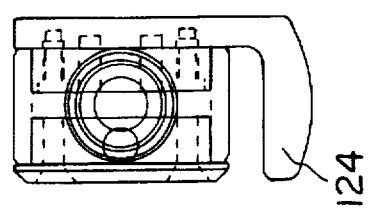
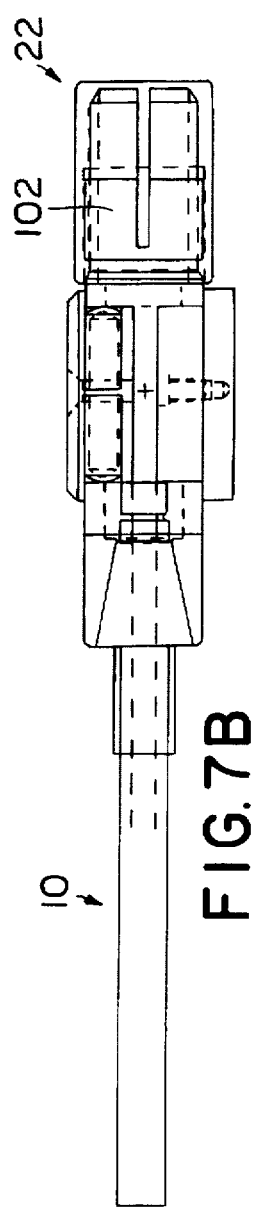
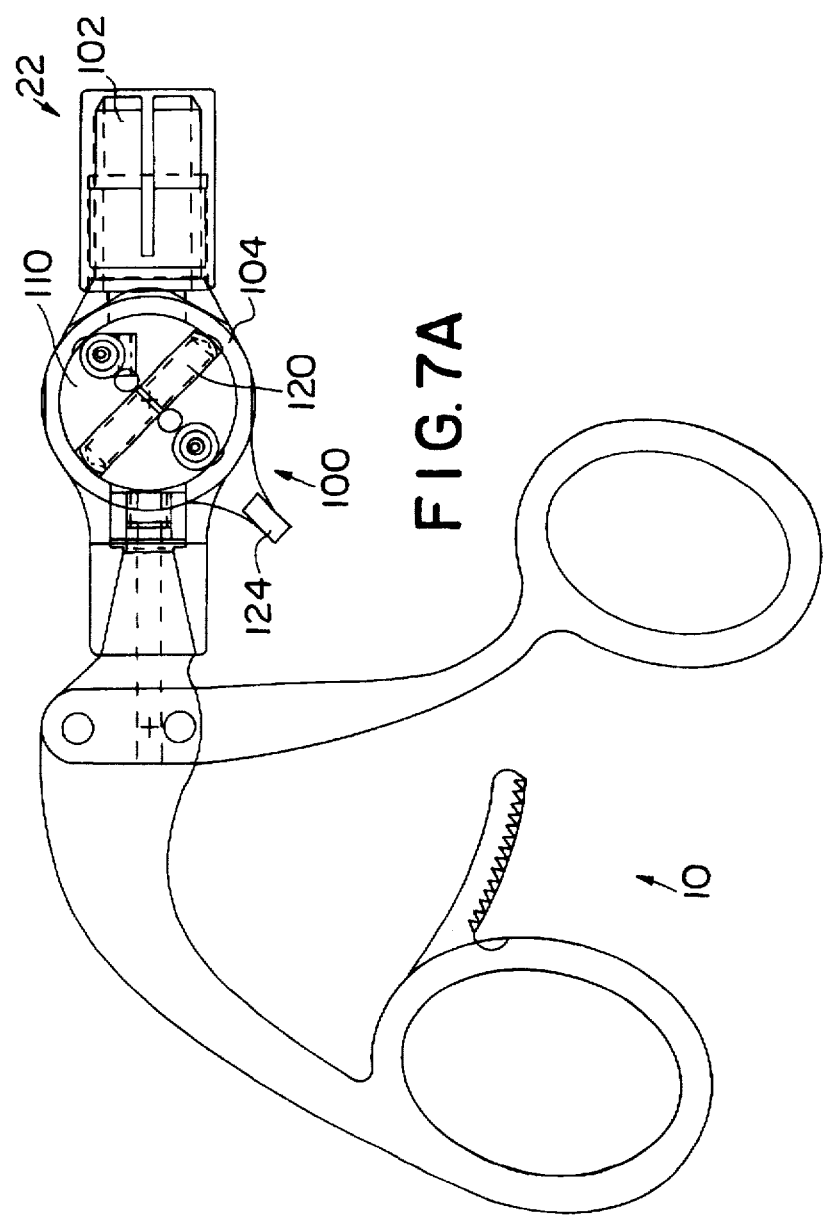

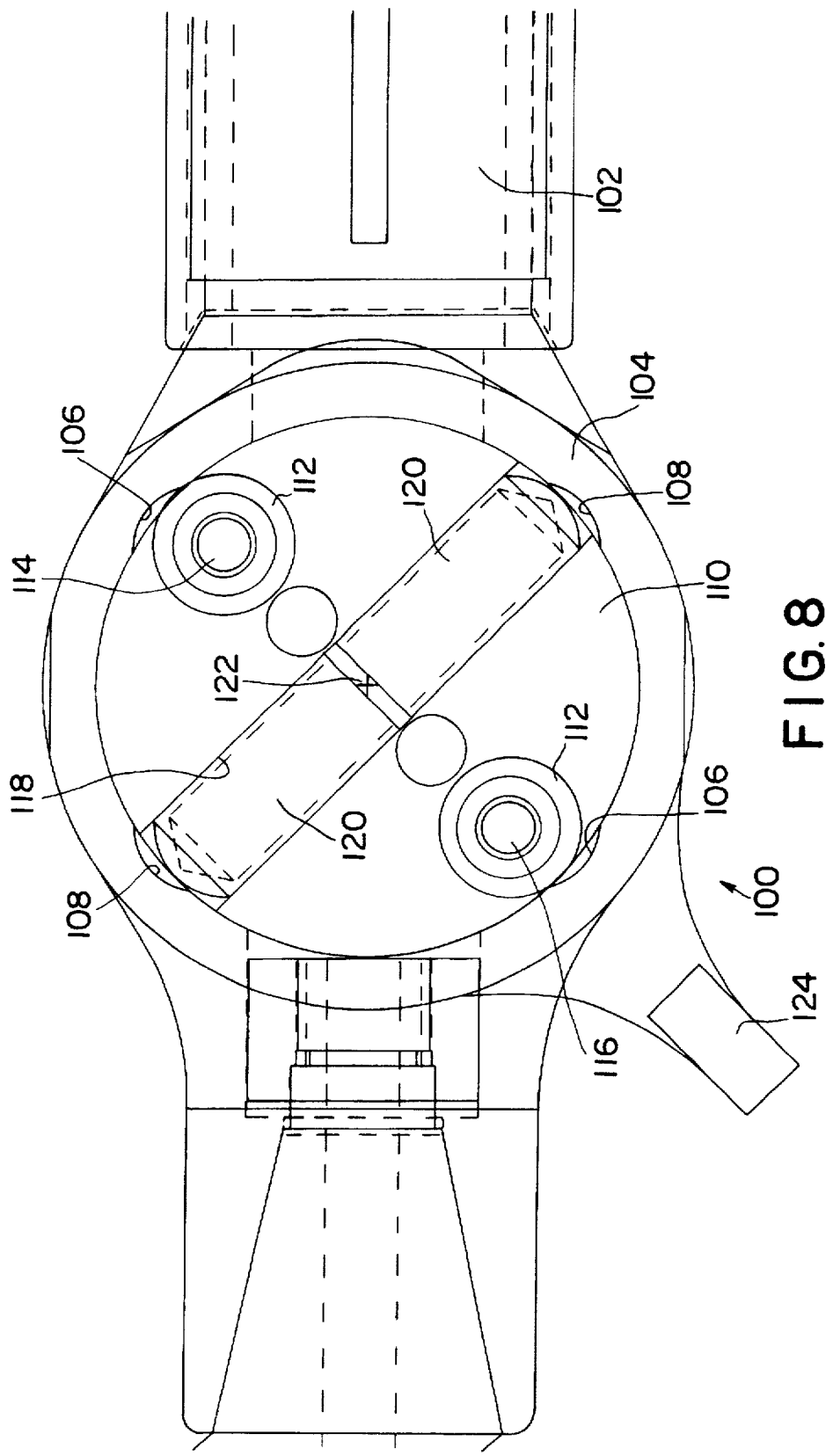

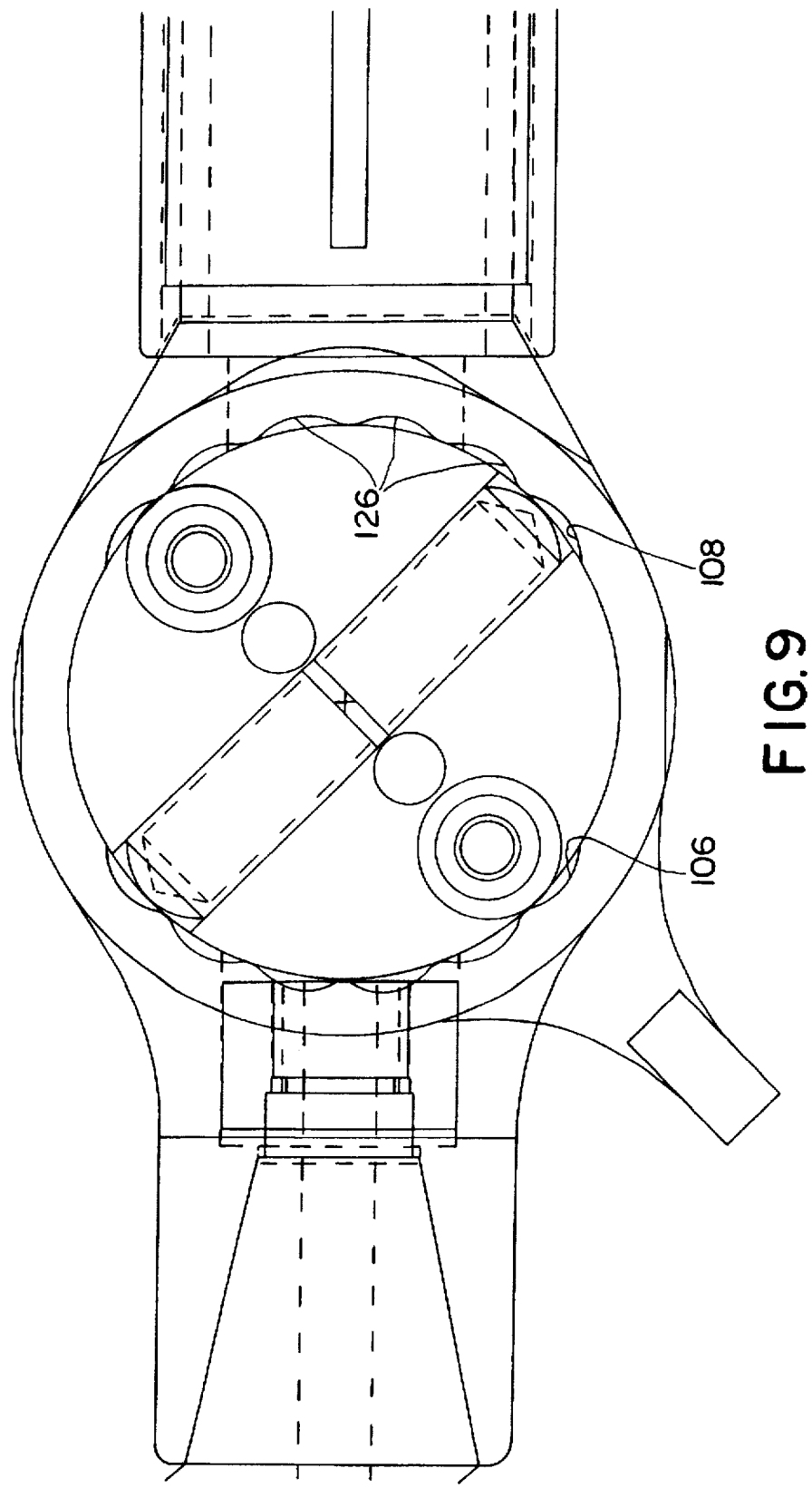

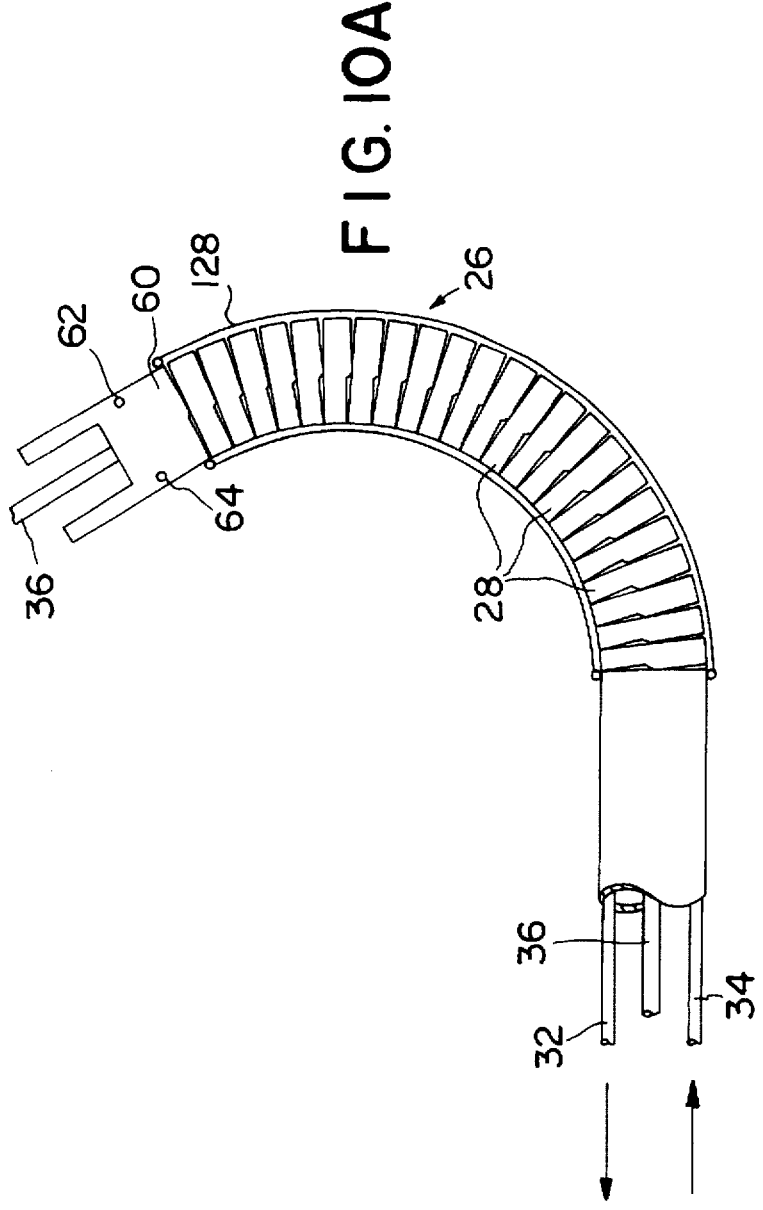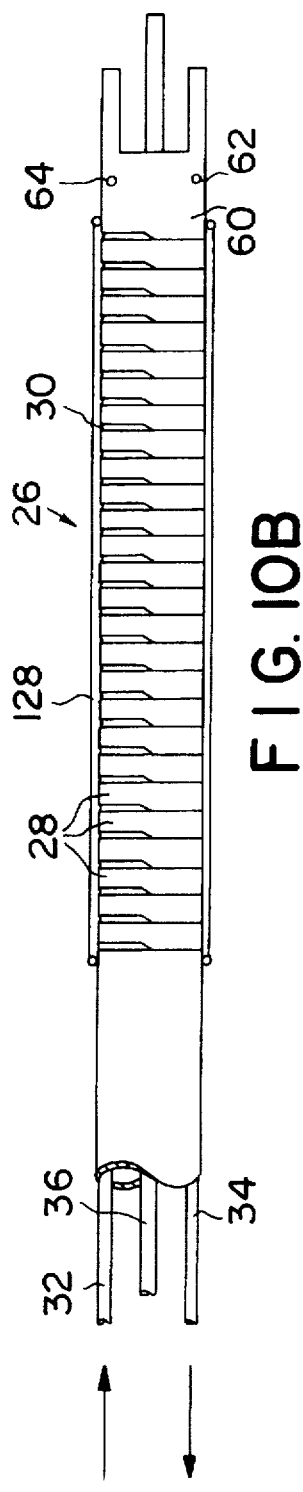

1

SURGICAL INSTRUMENT WITH STEERABLE DISTAL END

FIELD OF THE INVENTION

This is a continuation of application Ser. No. 08/254,900, filed Jun. 6, 1994, now abandoned.

The present invention relates generally to miniature surgical instruments and instrument systems, and, more particularly, to such instruments and systems as are used, e.g., in endoscopic surgery, including, forceps, graspers, needle holders, scissors, scalpels, trocars and punches.

BACKGROUND OF THE INVENTION

The present invention relates to micro-instruments, i.e., articulating hand held instruments used in micro-surgery and various types of surgical instruments, such as are used, e.g., in endoscopic surgery, including, e.g., as to endoscopy and other fields, forceps, graspers, needle holders, scissors and punches differentiated by their working tip designs, but using a common handle and tubular shafts, varying in length and/or diameter. The instruments can comprise scissors-handle-actuators, so-called cigar handle linear or rotary activators, or other actuators, with push or pull force application design modes.

The following discussion of the invention focuses on instruments required for endoscopic usage (minimally invasive procedures) and more particularly punches, scissors and graspers used in laparoscopic surgical procedures, and to other surgical instruments and non-surgical instruments.

Recent generations of enhanced miniaturization of endoscopic instruments have encountered the problem of being unable to reach certain areas because they were not bendable or flexible or did not articulate in a manner most useful for the surgeon. On current hand held medical instruments from the hand held portion to the distal end, the instruments are normally of a straight rigid design allowing the distal end to pass through a cannula to the work site.

In this field it is frequently difficult for the surgeon to obtain access to a particular portion of a body part due to the limitations of the instruments which are used. In an attempt to overcome this, a flexible forceps is disclosed in U.S. Pat. No. 3,895,636, which has a flexible shaft in the form of a thin solid rod of wire wound into the form of a hollow spring.

U.S. Pat. No. 5,209,747 discloses an adjustable angle medical forceps which has jaws mounted on a shaft and which shaft rotates about the main shaft so that the jaws can be rotated to be at different angles to the main rod.

U.S. Pat. No. 5,254,130 discloses a surgical device having a flexible end. However, such devices have not been adequate. It is a principal object of the invention to provide micro-instruments of the classes described above which have steerable distal effector ends to provide the surgeon with great flexibility in reaching body parts which are difficult to reach.

SUMMARY OF THE INVENTION

These and other objects are accomplished by a surgical instrument which has means for permitting steering of the end effector assembly. Once the distal end passes through the cannula the distal end may be moved radially away from a straight linear line in a steerable manner, controlled from the hand held portion of the instrument thereby allowing the distal end to operate in three dimensions as differentiated from the standard one dimension.

The mechanism is made of standard end effectors attached to an intermediate section which bends in a desired manner and which attaches the end effector to the handle and shaft sections of the instrument. The section which provides steering is constructed of a plurality of similar parts adjacent to one another and each of which has a specially shaped surface which allows the parts to be held together so that they are inclined with respect to each other thereby forming a curve in the section. Since the shaft on which these parts are connected can move into any angular position, the end effectors can be placed into any angular position once the instrument has been introduced into the patient's body. Wires which extend to the handle area control the inclining action of the parts. In the case of a biopsy, grasping jaws, after securing a specimen from a bent instrument, can be straightened and then removed from the patient's body through the cannula with the specimen intact.

Other objects, features and advantages will be apparent from the following detailed description of preferred embodiments taken in conjunction with the accompanying drawings in which:

BRIEF DESCRIPTION OF THE DRAWINGS

FIG. 1A is a side elevational view of a surgical instrument of the type to which the present invention belongs.

FIG. 1B is a plan view of the surgical instrument shown in FIG. 1A.

FIG. 2A is a side elevational view of a surgical instrument of the present invention showing the bendable section and the effector end of the instrument.

FIG. 2B is a plan view of the surgical instrument shown in FIG. 2A with the bendable section in bent condition.

FIG. 4A is a side elevational view, partly in section, showing the bendable section of the surgical instrument in bent condition.

FIG. 4B is a side elevational view, partly in section, showing the bendable section of the surgical instrument in straight condition.

FIG. 7A is a partial elevational view partly in section of a modified instrument showing another embodiment of the invention.

FIG. 7B is a plan view of the instrument shown in FIG. 7A.

FIG. 7C is a side elevation of the instrument shown in FIGS. 7A and 7B.

FIG. 8 is a detailed sectional view of a detent mechanism used to hold the wires in place.

FIG. 9 is a detailed sectional view of a modified detent mechanism.

FIG. 10A is a side elevational view, partly in section, showing the bendable section in modified form used on a surgical instrument in bent condition.

FIG. 10B is a side elevational view, partly in section, showing the bendable section of the instrument of FIG. 10A in straight condition.

DETAILED DESCRIPTION OF PREFERRED EMBODIMENTS

Figure 3A:
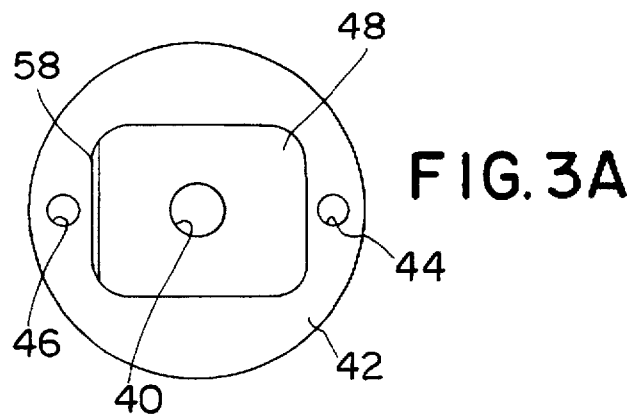
FIG. 3A is a plan view of one element of the bendable section of the surgical instrument.

FIGS. 1A and 1B show a handle assembly 10 of an articulating, hand-held instrument 12 of a straight rigid design having a distal articulating assembly or end effector 14 of a grasping type, such as that used in surgery, electronic assembly and like applications. Such an instrument may be as described, for example, in U.S. Pat.No. 4,712,545, 4,043, 343, and 1,754,806, but with a modified end and attachment base. It includes a fixed handle section 16, and an articulating handle portion 18. The grasping elements 20 of the handle portions are of closed-loop design.

The present invention is shown in FIGS. 2A and 2B which includes handle assembly 10, instrument 12, end effector 14, the end effector assembly 14 being steerable. The steering mechanism is made of standard end effectors attached to an actuating mechanism It also has a turnable device to rotate the end effector into a desired angular position after it has been introduced into a patient's body. It provides for rotating the end effector 14 about the longitudinal axis of the instrument. Such a mechanism is disclosed in copending application, Ser. No. 08/043,185, filed Apr. 6, 1993, and the disclosure thereof is incorporated herein by reference. Thus, the medical instrument 12 has a steerable distal end 14.

Once the distal end 14 passes through a cannula in the patient's body, the present invention allows the distal end 14 to move radially away from a straight linear line in a controlled steerable manner. It is controlled from the handle portion and allows the distal end to operate in three dimensions.

The handle 10, has a steering knob 22, attached to a middle section 24, which is connected to a bendable, steerable section 26, which is connected to a distal operating end 14 having jaws 27 or other similar devices. The bendable, steerable section is disposed close to the distal operating end. The bendable section 26 is made of a plurality of individual parts 28 (see FIGS. 4A and 4B) which are the same size and shape. When they are stacked together they allow a certain amount of angular movement between adjacent ones. The angular movement is permitted due to a cut-out portion 30 as will be described in more detail below.

There are three wires 32, 34 and 36, although element 36 could be a control rod. Wires 32 and 34 on the outside move and lock the individual parts 28, while the third wire, or rod, 36 runs through the center and controls the distal tips that do the cutting, grabbing, punching and the like. The center cable or rod 36 stays in the same relative position to the front tips 27 (see FIGS. 2A and 2B) and handle portion 10 during use of the bendable joint or section 26.

Figure 3B:
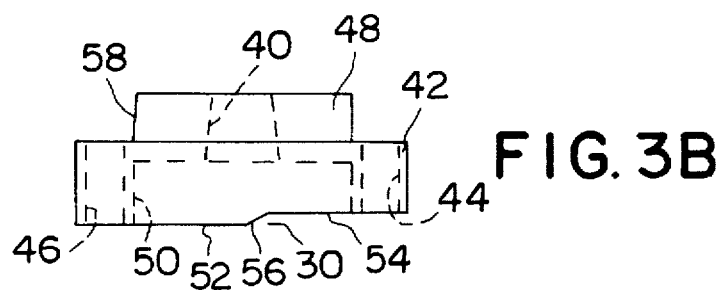
FIG. 3B is a front elevational view of the element shown in FIG. 3A.
Figure 3C:
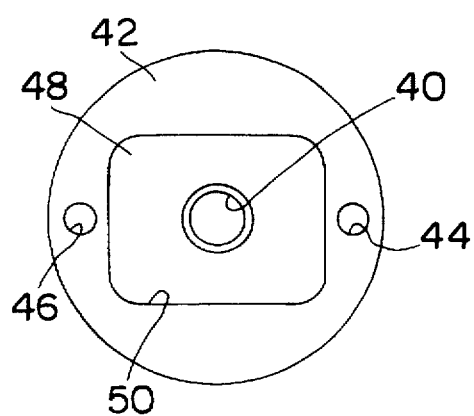
FIG. 3C is a bottom elevational view of the element shown in FIGS. 3A and 3B.
Figure 3D:
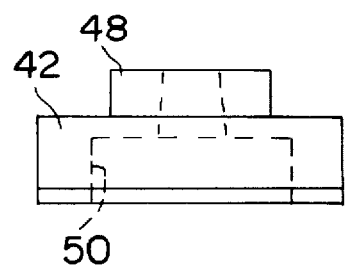
FIG. 3D is a side elevational view of the element shown in FIGS. 3A, 3B and 3C.
Figure 5A:
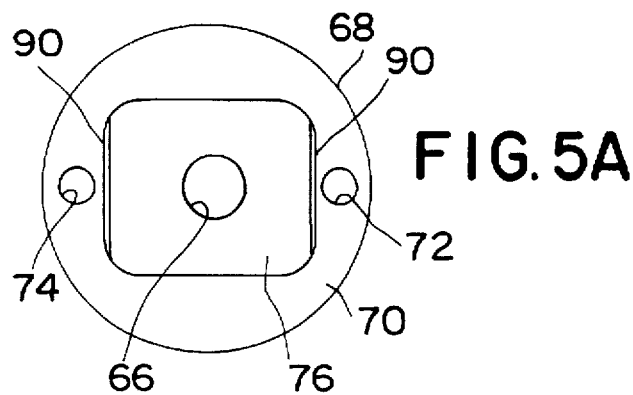
FIG. 5A is a plan view of one element of the bendable section of another embodiment of the surgical instrument.
Figure 5B:
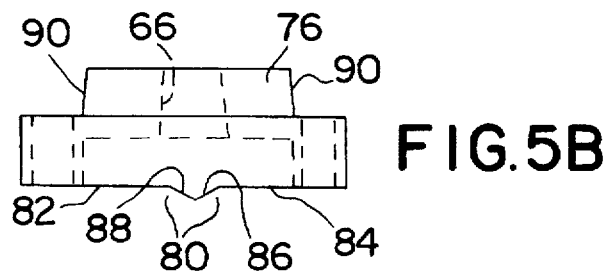
FIG. 5B is a front elevational view of the element shown in FIG. 5A.
Figure 5C:
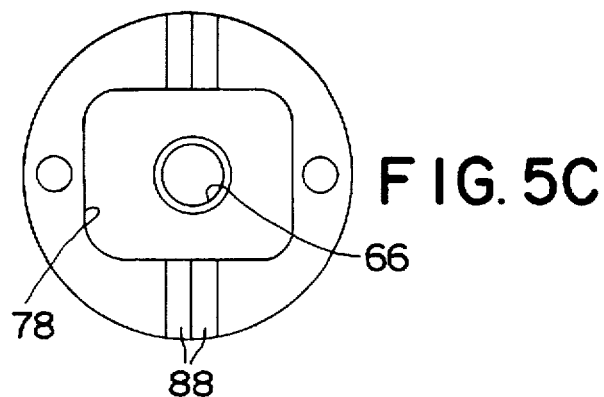
FIG. 5C is a bottom elevational view of the element shown in FIGS. 5A and 5B.
Figure 5D:
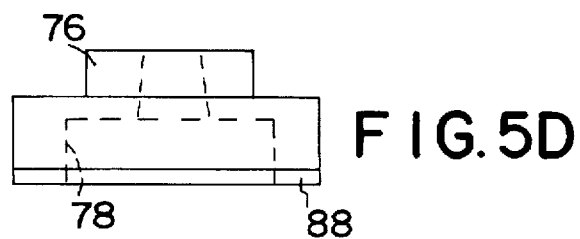
FIG. 5D is a side elevational view of the element shown in FIGS. 5A, 5B and 5C.

There is a central bore 40 (see FIGS. 3A, 3B and 3C) in each part 28 (see FIGS. 4A and 4B) through which cable or rod 36 fits to allow for a push and pull or rotatable actuator element to operate the effectors from the driver or handle area. The bore 40 is conical in shape. The joint will turn in only one plane because of the restriction of rotation of one part 28 to the next. This will allow the individual segments when assembled to move from a straight linear line to a radial curve in one direction only. The surgeon can rotate the entire distal end including the segment section and also use the device to move the distal end radially from a straight position.

Each stacked part or element 28 is constructed in a similar manner as shown in FIGS. 3A, 3B, 3C and 3D. The basic portion 42 is a disk shape and thus is round. Near the outer edge and 180 degrees apart are two straight bores 44 and 46 through which the control wires 32 and 34 are situated. Each element 28 has a rectangular extension 48 which projects from the disk shaped basic portion 42. The disk shaped basic portion 42 is hollowed out in the center on the side opposite the extension 48 to form a cavity 50. The cut-out 30 in the bottom surface of the disk shaped basic portion 42 is formed by a first end surface 52 and a second end surface 54 at the bottom surface of the element and which surfaces are parallel but offset from each other due to an inclined surface 56 connecting them. The extension 48 is slightly smaller than cavity 50 so that the extension of the adjacent element will extend into the cavity of the element. Furthermore, one side of the extension48, and this is the side where the first end surface 52 is located, is inclined at 58 as shown most clearly in FIG. 3B.

Thus, when a plurality of elements 28 are aligned with the parts in the same position, the extensions 48 project into the cavities 50 of adjacent elements. All the inclined surfaces 56 are aligned and so are the first end surfaces 52 and second end surfaces 54. When wire 34 (which is connected to an element connector 60 at connection point 62, which is the side on which the inclined surface 58 is disposed and on the side opposite where the cut-outs 30 are located) is moved in the direction of the arrow in FIG. 4B, the first end surfaces 52 of the elements are held together and the meeting parallel surfaces force them into aligned positions so that this section is straight as shown in FIG.4B. When wire 32, which is connected to element connector 60 at connection point 64, is moved in the direction of the arrow shown in FIG. 4A, wire 34 is moved in the direction of the arrow shown in FIG. 4A and the section is moved into the bent position shown in FIG. 4A.

The instrument, in the straight position as shown in FIG. 4B, is introduced into a patient's body through a cannula. When the surgeon needs to steer the distal end of the instrument in a particular direction out of this straight line position shown in FIG. 4B, he rotates the steerable knob 22 until the cutout side of the instrument faces the direction in which he or she wants to steer the distal end. The surgeon then moves wire 32 in the direction of the arrow shown in FIG. 4A and the instrument moves out of the straight line position as shown in this FIG. The control wire 36 is then used to move the end effector as desired.

Thus the bendable joint or section is made up of a number of individual pieces being the same size and shape which, when stacked together, allow a distinct amount of angular movement between any of them. The three wires or cables extend through the segments, the two outer ones moving and locking the individual pieces. The third runs through the center and controls the distal tips that are cutting, grabbing, punching, etc. The center cable stays in the same relative position to the front tips and handle portion during use of the bendable joint. Also, the central hole, through which the cable fits, allows for a push-pull or rotatable actuator element to operate the effectors from the driver. The joint will turn in only one plane because of the restriction of rotation of one piece to the next. The current configuration would allow the individual segments, when assembled, to move from a straight line to a radial curve in one direction only. With the feature of copending commonly assigned application Ser. No. 08/043,185 for a Surgical Instrument With Rotation, this allows the surgeon user to rotate the entire distal end including the segment section and also use the new invention to move the distal end radially from a straight position.

A modification of the element which allows the segment section to articulate in both directions from a center position by having two cut-out portions 180 degrees apart on each part is shown in FIGS. 5A, 5B, 5C and 5D.

There is a central bore 66 in each part 68 through which cable 36 fits to allow for a push and pull or rotatable actuator element to operate the effectors from the driver or handle area. The bore 66 is conical in shape. The joint will turn in only one plane because of the restriction of rotation of one part 68 to the next. This will allow the individual segments when assembled to move from a straight line to a radial curve in one direction only. The surgeon can rotate the entire distal end including the segment section and also use the device to move the distal end radially from a straight position.

Each stacked part or element 68 is constructed in a similar manner as shown in FIGS. 5A, 5B, 5C and 5D. The basic portion 70 is a disk shape and thus is round. Near the outer edge and 180 degrees apart are two straight bores 72 and 74 through which the control wires 32 and 34 are situated. Each element 68 has a rectangular extension 76 which projects from the disk shaped basic portion 70. The disk shaped basic portion 70 is hollowed out in the center on the side opposite the extension 76 to form a cavity 78. The cut-outs 80 in the bottom surface of the disk shaped basic portion 70 is formed by a first end surface 82 and a second end surface 84 at the bottom surface of the element and which surfaces are aligned with each other. There is a projection 86 formed by two inclined surfaces 88 connected together. The extension 76 is slightly smaller than cavity 78 so that the extension of the adjacent element will extend into the cavity of the element. Furthermore, two sides of the extension, inclined at 90 are shown most clearly in FIG. 5B.

Thus, when a plurality of elements 68 are aligned with the parts in the same position, the extensions project into the cavities of adjacent elements. When wire 34, which is connected to an element connector 60 at 62, which is the side on which one of the inclined surfaces 90 are disposed is moved in the direction of the arrow in FIG. 4B, the first end surfaces 82 of the elements are held together and depending upon how far the wire is moved, the elements will be parallel, in which condition the bendable section is straight, or will be moved so that the surfaces 82 are moved closer together, in which condition the bendable section will flex in the direction of the aligned end surfaces 82. When wire 32, which is connected to an element connector 60 at 64, which is the side on which the other of the inclined surfaces 90 is disposed is moved opposite the direction of the arrow shown in FIG. 4B, the second end surfaces 84 of the elements are held together and, depending upon how far the wire is moved, the elements will be parallel, in which condition the bendable section is straight, or will be moved so that the surfaces 84 are moved closer together, in which condition the bendable section will bend in the direction of the aligned end surfaces 84, which is 180 degrees from the direction when the wire 34 is moved.

The instrument, in the straight position as shown in FIG. 4B, is introduced into a patient's body through a cannula. When the surgeon needs to steer the distal end of the instrument in a particular direction out of this straight line position shown in FIG. 4B, he rotates the steerable knob 22 until one of the cutout sides of the instrument faces the direction in which he wants to steer the distal end. He then moves wire 32 or 34 in the direction of the arrow and the instrument moves out of the straight line position into one of two directions 180 degrees apart. The control wire 36 is then used to move the end effector as desired.

Thus, the bendable joint or section is made up of a number of individual pieces being the same size and shape which, when stacked together, allow a distinct amount of angular movement between any of them. The three wires or cables extend through the segments, the two outer ones moving and locking the individual pieces. The third runs through the center and controls the distal tips that are cutting, grabbing, punching, etc. The center cable stays in the same relative position to the front tips and handle portion during use of the bendable joint. Also, the central hole, through which the cable fits, allows for a push-pull or rotatable actuator element to operate the effectors from the driver.

The joint will turn in only two planes because of the restriction of rotation of one piece to the next. The current configuration would allow the individual segments, when assembled, to move from a straight linear line to a radial curve in two directions only.

Figure 6C:
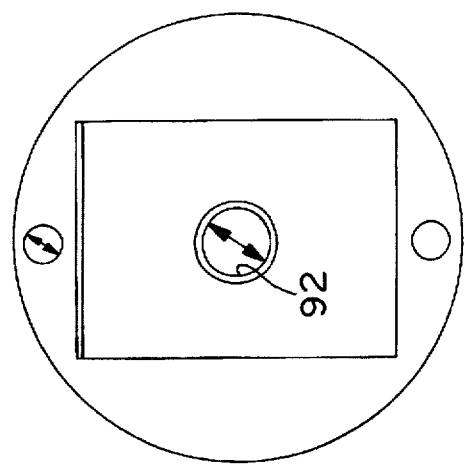
FIG. 6C is a plan view of the element shown in FIGS. 6A and 6B.
Figure 6B:
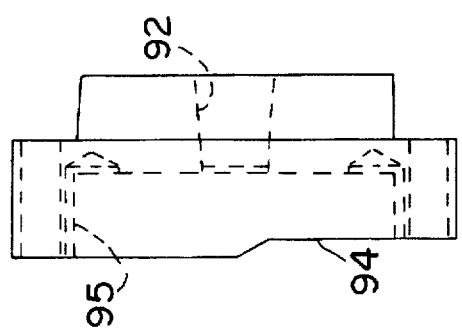
FIG. 6B is a front elevational view of the element shown in FIG. 6A.
Figure 6A:
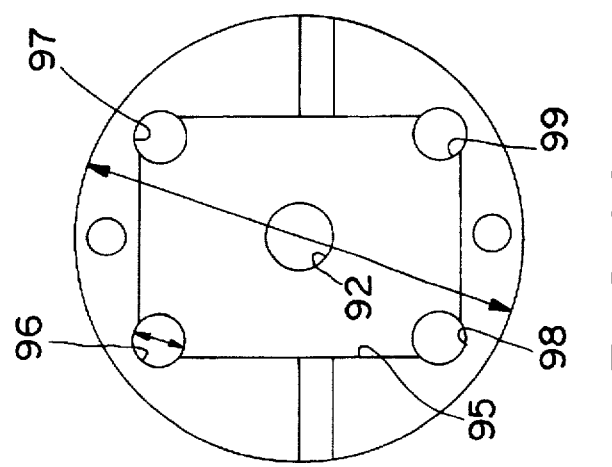
FIG. 6A is a bottom elevational view of a modified form of the element shown in FIGS. 3A, 3B, 3C and 3D.
Figure 11:
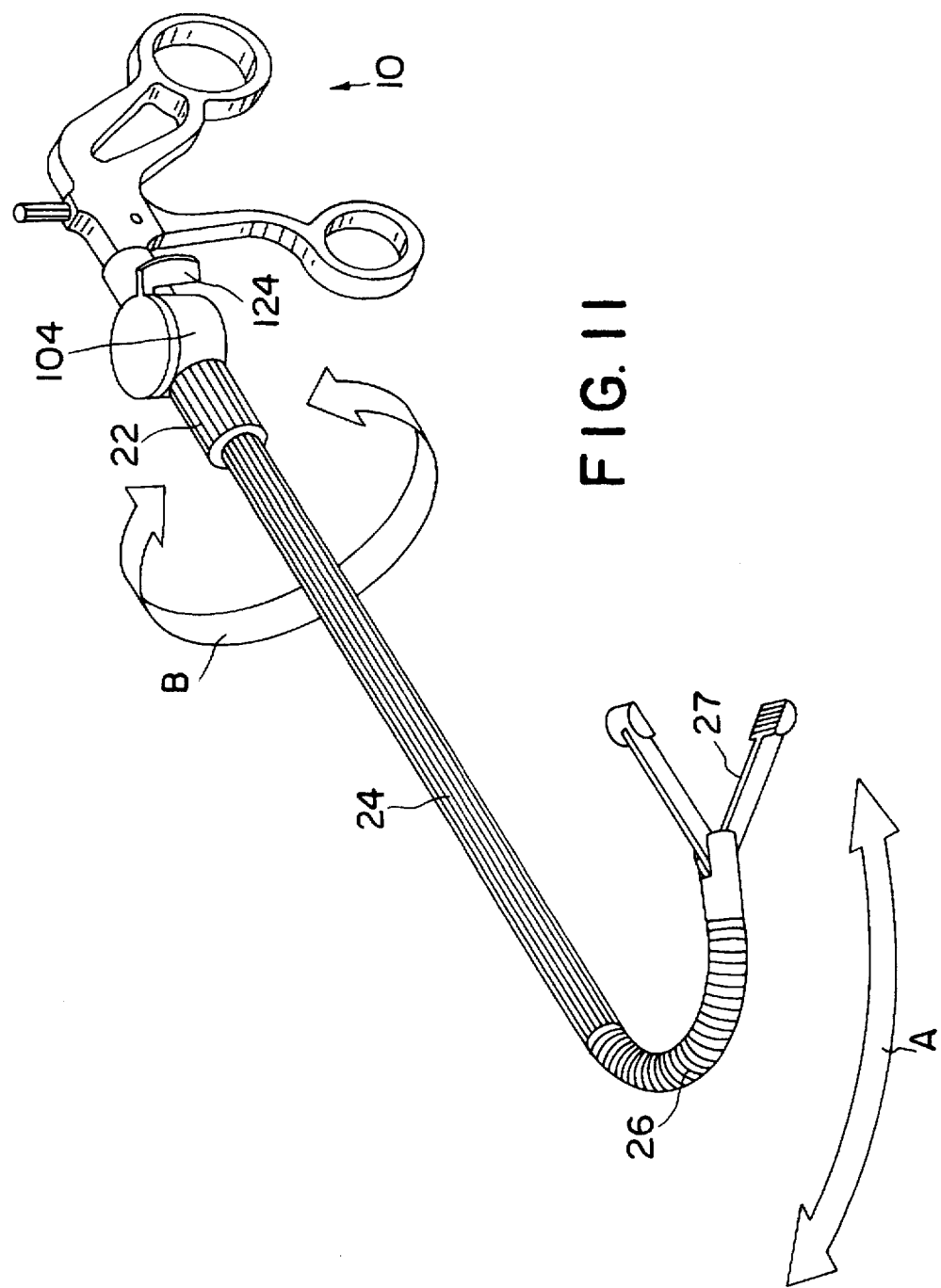
FIG. 11 is an isometric view of the instrument of the present invention.

A modification of the element shown in FIGS. 3A, 3B, 3C and 3D is shown in FIGS. 6A, 6B and 6C in which only the differences are labeled with lead lines and reference numerals. The bore 92 through the center of the element in this embodiment tapers in the opposite direction than bore 40 in the first embodiment. Also, the bore has a chamfer at 94. There are 4 counter bores 96, 97, 98 and 99 at the corners of the cavity 95.

FIGS. 7A, 7B, 7C and 8 show a modified instrument showing another embodiment of the invention. There is a handle 10 as well as a steering knob device 22 (see FIGS. 2A and 2B). However, between them is a control and restraining mechanism 100 for the control wires 32 and 34 (see FIGS. 4A and 4B) which are used to bend the bendable section 26 (see FIGS. 2 A, 2B, 4A and 4B) into extreme positions as well as intermediate positions. The wire 32 can be pulled to any number of intermediate positions to provide as much or little bend as desired. To straighten the bendable section 26, one pulls the wire 34 to an extreme position and the surgeon knows without looking that the section is straight and can be removed from the patient's body through the cannula. The angular position of the end effector is controlled by the steering knob device which includes a cylinder 102 which can be rotated to move the end effector 27 (see FIGS. 2A and 2B) into the desired position. This cylinder 102 is located close to the handle 10 so that it and the control and restraining mechanism 100, as well as the end effector 27 can be operated by the surgeon with one hand.

The control and restraining mechanism 100, includes a cylindrical housing 104 having two sets of grooves 106 and 108 in the interior of the cylindrical walls at the two extreme ends of the movement of the wires. Within the housing 104 is a rotor 110 which rotates within the housing 104. The rotor 110 includes wire holding elements 112 to hold the wires in position and thus the bendable section in position. Wire 32 is fixed in the rotor at rotor connection 114 while wire 34 is fixed in the rotor at rotor connection 116 spaced 180 degrees therefrom. There is a cylindrical bore 118 in rotor 110 in which are two biased cylinders 120 having a spring 122 between them to bias them outwardly toward the walls of the housing 104. The outer surfaces of cylinders 120 are smooth and slightly curved so they act like detents to hold the rotor into position when the cylinders are in the detents in the two extreme positions. In one of these positions the cylinders 120 are in the grooves 106 and in the other extreme position the cylinders are in the grooves 108. Thus, a 90 degree movement is all that is needed to move the bendable section between the straight and the most extreme bent position.

The control and restraining mechanism 100 which includes the cylinder 102 of the steering knob device 22 are both mounted for rotation together so that when the cylinder has its angular position changed, such as when the surgeon is positioning the end effector angularly, the wire control device rotates therewith.

Thus, when it is desired to change the position of the bendable section from straight to bent or vice versa, the lever 124 is moved 90 degrees which rotates the rotor 110 to move the control wires 32 and 34.

FIG. 9 is a detailed sectional view of a modified detent mechanism in which there are many additional grooves 126, in positions between the extreme position grooves 106 and 108 so that detents hold the position of the wire control even between the two extreme positions.

The control wires can be held in place to maintain the bendable section in a desired position by having the wires held by a resistance, possibly with a control knob or a brake mechanism.

FIGS. 10A and 10B show the bendable section in modified form used on a surgical instrument in bent condition and in straight condition. In this embodiment there is a sheath 128 composed of resilient material which surrounds at least the bendable section to protect it and prevent tissue from the patient's body from becoming entrapped in the openings between the elements.

There are two different embodiments of the actuating mechanism. In one it articulates with a push, and in the second it is reverse and the tip articulates with a pull which has the advantage of increasing the rigidity of the assembly.

The end effector does not have to be controlled with a push-pull motion, but can be controlled by a rotational motion from the handle.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A medical instrument with a steerable distal end, comprising:
   a. a handle for actuating the instrument, said handle being capable of having attached thereto a plurality of tensioning members;
   b. a distal operating section for performing a medical procedure and actuated from said handle, said distal operating section, being capable of having attached thereto a plurality of tensioning members;
   c. a middle section connecting said handle with said operating section and defining a central lumen throughout the length of said middle section, at least a portion of said middle section being bendable into a smooth curve from, the proximal end of the middle section to the point where it joins the distal operating section;
   d. said bendable portion being arranged and constructed to be steerable for permitting the operating section to be controlled in direction at an angle in three dimensions with respect to the axis of the middle section from a position along said axis separated from said bendable portion; and
   e. means for rotating the distal operating-section into any desired angular position wherein said plurality of tensioning members are attached at their respective first ends to said handle and at their respective second ends to said distal operating section such that all of said tensioning members pass through said central lumen and further such that actuation of said handle operates on said plurality of tensioning members such that said bendable portion is urged to bend, thereby causing said distal operating section to be steered.

2. A medical instrument with a steerable distal end, comprising:
   a. a handle for actuating the instrument;
   b. a distal operating section for performing a medical procedure and actuated from said handle;
   c. a middle section connecting said handle with said operating section, at least a portion of said middle section being bendable into a smooth curve from the proximal end of the middle section to the point where it joins the distal operating section;
   d. said bendable portion being arranged and constructed to be steerable for permitting the operating section to be controlled in direction at an angle in three dimensions with respect to the axis of the middle section; and
   e. means for rotating the distal operating section into any desired angular position.

3. A medical instrument with a steerable distal end, comprising:
   a. a handle for actuating the instrument, said handle being capable of having attached thereto a plurality of tensioning members;
   b. a distal operating section for performing a medical procedure and actuated from said handle, said distal operating section being capable of having attached thereto a plurality of tensioning members;
   c. a middle section connecting said handle with said operating section and defining a central lumen throughout a first portion of its length and having a second portion comprising a plurality of similarly shaped stackable members that each define a plurality of lumens and being arranged so that said plurality of lumens are in alignment such that a like plurality of tensioning members, each having a first and a second end, may be disposed therethrough, said stackable members permitting angular movement between them and thereby allowing for bending movement of the bendable portion, so that, on actuation by said handle, they are bendable;
   d. said bendable portion being arranged and constructed to be steerable for permitting the operating section to be controlled in direction at an angle with respect to the axis of the middle section from a position along said axis separated from said bendable portion; and
   e. means for rotating the distal operating section into any desired angular position wherein said plurality of tensioning members are attached at their respective first ends to said handle and at their respective second ends to said distal operating section such that each of said tensioning members passes through one of said lumens formed by alignment of said stackable members and all of said tensioning members pass through said central lumen and further such that actuation of said handle operates on said plurality of tensioning members such that said plurality of stackable members is urged to bend, thereby causing said distal operating section to be steered.

4. A medical instrument with a steerable distal end, comprising:
 a. a handle for actuating the instrument;
 b. a distal operating section for performing a medical procedure and actuated from said handle;
 c. a middle section connecting said handle with said operating section, at least a portion of said middle section being bendable; and
 d. said bendable portion being arranged and constructed to be steerable for permitting the operating section to be controlled in direction at an angle with respect to the axis of the middle section, said bendable portion including a plurality of a single type of similarly shaped stacked elements permitting angular movement between them and thereby allowing for bending movement of the bendable portion, said elements being stacked against one another and one side thereof of each of them having a portion removed to allow angular movement between adjacent elements.

5. A medical instrument as defined in claim 4, wherein the removed portion of said elements are all aligned so that the angular movement always takes place along the aligned axis.

6. A medical instrument as defined in claim 5, wherein each stacked element has an extension on one side and a cavity slightly larger than the extension on the other side, and the extension of each element is disposed in the cavity of the adjacent element.

7. A medical instrument as defined in claim 6, wherein the cavity and extension are shaped so that the extension cannot rotate within the cavity.

8. A medical instrument with a steerable distal end, comprising:
 a. a handle for actuating the instrument;
 b. a distal operating section for performing a medical procedure and actuated from said handle;
 c. a middle section connecting said handle with said operating section, at least a portion of said middle section being bendable into a smooth curve from the proximal end of the middle section to the point where it joins the distal operating section;
 d. said bendable portion being arranged and constructed to be steerable for permitting the operating section to be controlled in direction at an angle in three dimensions with respect to the axis of the middle section; and
 e. control means
wherein control means includes means for rotating the distal operating section into any desired angular position about the longitudinal axis of said middle section.

9. A medical instrument as defined in claim 8 wherein said control means includes means for securing the control means in any position to which it is set by a user.

10. A medical instrument as defined in claim 8 wherein said control means includes wires disposed from the handle to the end of the bendable portion whereby the bending movement of the bendable portion can be controlled by manipulation of said wires.

11. A medical instrument as defined in claim 10 wherein said control means further includes means for securing the wires in the position into which they are placed by a user.

12. A medical instrument as defined in claim 11 wherein said securing means includes a brake.

13. A medical instrument as defined in claim 8, wherein said control means are located adjacent said handle and are constructed and arranged so that said control means can be operated by the user with one finger.

14. A medical instrument with a steerable distal end, comprising:
 a. a handle for actuating the instrument;
 b. a distal operating section for performing a medical procedure and actuated from said handle;
 c. a middle section connecting said handle with said operating section, at least a portion of said middle section being bendable;
 d. said bendable portion being arranged and constructed to be steerable for permitting the operating section to be controlled in direction at an angle with respect to the axis of the middle section;
 e. control means for controlling the direction of movement of the bendable portion in three dimensions whereby the distal end may be positioned in any place on or off of the longitudinal axis of the middle section, said control means including means for securing the wires in the position into which they are placed by a user;

said securing means includes a turnable restraint having detents at the extreme position in each direction.

15. A medical instrument as defined in claim 14 wherein said turnable restraint has a plurality of detents between the extreme positions.

16. A medical instrument with a steerable distal end, comprising:
 a a handle for actuating the instrument, said handle being capable of having attached thereto a plurality of tensioning members;
 b. a distal operating section for performing a medical procedure and actuated from said handle, said distal operating section being capable of having attached thereto a plurality of tensioning members;
 c. a middle section connecting said handle with said operating section and defining a central lumen throughout a first portion of its length and having a second, bendable portion comprising a plurality of similarly shaped stackable members that each define a plurality of lumens and being arranged so that said plurality of lumens are in alignment such that a like plurality of tensioning members, each having a first and a second end, may be disposed therethrough, said stackable members permitting angular movement between them and thereby allowing for bending movement of the bendable portion, so that, on actuation by said handle, they are bendable;
 d. said bendable portion being arranged and constructed to be steerable for permitting the operating section to be controlled in direction at an angle with respect to the axis of the middle section from a position along said-axis separated from said bendable portion
wherein said plurality of tensioning members are attached at their respective first ends to said handle and at their respective second ends to said distal operating section such that each of said tensioning members passes through one of said lumens formed by alignment of said stackable members and all of said tensioning members pass through said central lumen and further such that actuation of said handle operates on said plurality of tensioning members such that said plurality of stackable members is urged to bend, thereby causing said distal operating section to be steered; and e. a sheath surrounding the elements forming the bendable portion.

17. A medical instrument as defined in claim 19 wherein the distal operating section has jaws for gripping, and the steerable means are constructed and arranged to be capable of being straight when the jaws are in closed position so that the instrument can be withdrawn from the patient while the bendable portion is in straight condition.

18. A medical instrument as defined in claim 16 wherein a sheath surrounds the bendable portion.

* * * * *